United States Patent
Bimmler et al.

(10) Patent No.: US 9,708,372 B2
(45) Date of Patent: Jul. 18, 2017

(54) AGONISTIC AUTOANTIBODIES TO THE ALPHA1-ADRENERGIC RECEPTOR AND THE BETA2-ADRENERGIC RECEPTOR IN ALZHEIMER'S AND VASCULAR DEMENTIA

(71) Applicants: E.R.D.E.-AAK-DIAGNOSTIK GMBH, Berlin (DE); MAX-DEL-BRUCK-CENTRUM FÜR MOLEKULARE MEDIZIN, Berlin (DE)

(72) Inventors: Marion Bimmler, Königs Wusterhausen Ot Zernsdorf (DE); Peter Karczewski, Berlin (DE); Petra Hempel, Berlin (DE)

(73) Assignees: E.R.D.E.-AAK-DIAGNOSTIK GMBH, Berlin (DE); MAX-DEL-BRUCK-CENTRUM FÜR MOLEKULARE MEDIZIN, Berlin (DE)

( * ) Notice: Subject to any disclaimer, the term of this patent is extended or adjusted under 35 U.S.C. 154(b) by 58 days.

(21) Appl. No.: 14/749,408

(22) Filed: Jun. 24, 2015

(65) Prior Publication Data

US 2015/0291661 A1 Oct. 15, 2015

Related U.S. Application Data

(62) Division of application No. 14/238,450, filed as application No. PCT/EP2012/063789 on Jul. 13, 2012, now abandoned.

(30) Foreign Application Priority Data

Aug. 12, 2011 (EP) .................................... 11177414

(51) Int. Cl.
| | |
|---|---|
| C07K 7/08 | (2006.01) |
| C07K 16/18 | (2006.01) |
| G01N 33/566 | (2006.01) |
| C07K 14/705 | (2006.01) |
| A61M 1/36 | (2006.01) |
| G01N 33/564 | (2006.01) |

(52) U.S. Cl.
CPC ............. *C07K 7/08* (2013.01); *A61M 1/3679* (2013.01); *C07K 14/70571* (2013.01); *C07K 16/18* (2013.01); *G01N 33/564* (2013.01); *G01N 33/566* (2013.01); *C07K 2317/75* (2013.01); *G01N 2800/2814* (2013.01); *G01N 2800/2821* (2013.01)

(58) Field of Classification Search
None
See application file for complete search history.

(56) References Cited

U.S. PATENT DOCUMENTS

| 2009/0181380 A1 | 7/2009 | Belouchi et al. |
| 2011/0166844 A1 | 7/2011 | Gustafsson et al. |

FOREIGN PATENT DOCUMENTS

| WO | WO 02/09374 A2 | 1/2002 |
| WO | WO 02/16431 A2 | 2/2002 |
| WO | WO 2005/109000 A2 | 11/2005 |
| WO | WO 2006/113602 A2 | 10/2006 |
| WO | WO 2009/090227 A2 | 7/2009 |

OTHER PUBLICATIONS

Google 2016 "definition of indicate" accessed from google.com on Oct. 14, 2016.*
Kunze 2010 "agonistic autoantibodies against the .alpha.1-adrenoceptor in patients with morbus alzheimer and vascular dementia" poster presentation abstract.*
Hwa et al. 1995 "Identification of critical determinants of $\alpha_1$-adrenergic receptor subtype selective agonist binding" *J Biol Chem* 270(39): 231189-23195.
Kunze, R. 2010 "Agonistic autoantibodies against the alpha1-adrenoceptor in patients with Morbus Alzheimer and vascular dementia" *Alzheimer's & Dementia: The Journal of the Alzheimer's Association* 6:4, S413 (Poster Abstract).
Lei et al. 2005 "Novel human alpha1a adrenoceptor single nucleotide polymorphisms alter receptor pharmacology and biological function" *Naunyn Schmiedebergs Arch Pharmacol* 371 (3): 229-239.
Ni, Y. et al. 2006 "Activation of $\beta_2$-adrenergic receptor stimulates $\gamma$-secretase activity and accelerates amyloid plaque formation" *Nature Medicine* 12: 1390-1396.
Karczewski, P. et al. 2012 "Agonistic autoantibodies to the $\alpha_1$-Adrenergic Receptor and the $\beta_2$-adrenergic receptor in Alzheimer's and vascular Dementia" *Scandinavian Journal of Immunology* 75: 524-530.

* cited by examiner

*Primary Examiner* — Adam M Weidner
(74) *Attorney, Agent, or Firm* — Knobbe, Martens, Olson & Bear, LLP (57) ABSTRACT

The invention relates to means for detecting, binding, removing and/or neutralizing agonistic antibodies associated with dementia, preferably Alzheimer's disease or vascular dementia.

15 Claims, 4 Drawing Sheets

SEQUENCE LISTING

```
<160> NUMBER OF SEQ ID NOS: 3

<210> SEQ ID NO 1
<211> LENGTH: 12
<212> TYPE: PRT
<213> ORGANISM: Homo sapiens

<400> SEQUENCE: 1

Leu Gly Tyr Trp Ala Phe Gly Arg Val Phe Cys Asn
1               5                   10

<210> SEQ ID NO 2
<211> LENGTH: 14
<212> TYPE: PRT
<213> ORGANISM: Homo sapiens

<400> SEQUENCE: 2

Pro Ala Pro Glu Asp Glu Thr Ile Cys Gln Ile Asn Glu Glu
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Ser Gly Lys Lys
1
```

AGONISTIC AUTOANTIBODIES TO THE ALPHA1-ADRENERGIC RECEPTOR AND THE BETA2-ADRENERGIC RECEPTOR IN ALZHEIMER'S AND VASCULAR DEMENTIA

FIELD OF THE INVENTION

The invention is based on autoimmune mechanisms that play a significant role in the pathogenesis of Alzheimer's and vascular dementia, whereby agonistic autoantibodies directed to the α1-adrenergic and the β2-adrenergic receptor contribute to vascular lesions and increased plaque formation.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 20985144_1.txt, the date of creation of the ASCII text file is Jun. 24, 2015, and the size of the ASCII text file is 1012 bytes.

BACKGROUND OF THE INVENTION

With increasing life expectance of humans in the industrialized countries age-correlated dementia increasingly becomes a social and economic problem. Among the different forms of dementia, Alzheimer's disease (AD) is the most common cause. Although recent research unraveled detailed molecular mechanisms of AD pathogenesis, the cause of the sporadic form is widely unknown, most likely because of its heterogeneous nature. Two proteins have been established as central pathomolecules, the plaque forming amyloid β, and the tangle composing hyperphosphorylated tau. Notably, the involvement of the $β_2$-adrenergic receptor ($β_2$-AR) in processing precursor proteins of amyloid-β was recently reported [1]. Activation of $β_2$-AR resulted in enhanced plaque formation. The most obvious risk factor of AD is ageing. Other risk factors include hypercholesterolemia, hypertension, atherosclerosis, coronary heart disease, smoking, obesity, and type 2 diabetes [2, 3]. There is evidence that the cognitive decline and central nervous system pathology may be secondary to pathologic alterations in the vasculature of AD patients' brain [4]. Epidemiological, clinical pharmacological, neuroimaging and pathological studies support the notion that vascular disorders are the primary cause of sporadic, non-genetic AD.

The second most common form of dementia in older adults is vascular dementia. Often AD and vascular dementia coexist in older patients. The causes of this form of dementia are different, often diffuse disorders all leading to vascular lesions. People who suffered from ischemic stroke developed dementia with a four-fold higher incidence than controls [5].

Adrenergic receptors (AR) belong to the superfamily of G protein-coupled receptors (GPCR), the most important cell surface receptors. AR mediate the action of catecholamines at the cellular level. They regulate numerous cellular functions such as muscle contraction including vascular tone. Circulating agonistic autoantibodies (agAAB) directed against AR have been found to be associated with different, mainly cardiovascular diseases in humans. It was shown that patients suffering from hypertension may contain agAAB predominantly to the $α_1$-adrenergic receptor ($α_1$-AR) or to the angiotensin II type 1 receptor [6-8]. There is growing evidence that these agAAB are of pathogenic relevance [9, 10]. In animal models it was shown that agAAB to the $α_1$-AR induce cellular remodeling and cause vascular damages [11-13]. Based on evidences of agAAB potency to cause vascular damages and of the crucial role of vascular disorders in AD and vascular dementia, investigation was undertaken to interrogate the involvement of GPCR related autoimmune mechanisms in this disease.

The invention discloses for the first time the presence of agAAB to the $α_1$-AR and $β_2$-adrenergic receptor ($β_2$-AR) in patients with moderate to mild dementia of the AD and vascular type.

SUMMARY OF THE INVENTION

The invention relates to means for detecting, binding, removing and/or neutralising agonistic antibodies associated with dementia, preferably Alzheimer's disease or vascular dementia. The invention therefore relates to peptides that are derived from targets of agonistic pathogenic autoantibodies, said peptides therefore binding and/or neutralizing the agonistic antibodies. The invention relates to recognition molecules that bind the agonistic antibodies associated with dementia, for example therapeutic antibodies that bind and neutralize the autoantibodies. The invention also relates to diagnostic methods and kits based on the inventive peptides and recognition molecules, solid phases and chromatography devices for apharesis-based treatment approaches, in addition to pharmaceutical compositions, which comprise the inventive peptides, recognition molecules or related nucleic acids.

Although primary causes of Alzheimer's and vascular dementia are unknown, the importance of preceding vascular lesions is widely accepted. Furthermore, there is strong evidence for the involvement of autoimmune mechanisms. The invention is based on the identification of agonistic autoantibodies directed at adrenergic receptors in the circulation of patients with mild to moderate Alzheimer's and vascular dementia. In 59% of these patients agonistic autoantibodies against the $α_1$-adrenergic receptor extracellular loop 1 and the $β_2$-adrenergic receptor extracellular loops 1 and 2 were identified. The majority of positive patients (66%) contained both types of autoantibodies in combination. In a control group of patients with neurological impairments others than Alzheimer's and vascular dementia, only 17% were found to harbor these autoantibodies. The autoantibodies to the $α_1$-adrenergic receptor interacted preferably with the extracellular loop1 of the receptor. They were further studied in IgG preparations from the column regenerate of a patient who underwent immunoadsorption. The $α_1$-adrenergic receptor autoantibodies specifically bound to the extracellular loop1 peptide of the receptor with an apparent $EC_{50}$ value of 30 nM. They mobilized intracellular calcium in a clonal cell line expressing the human form of the $α_1$-adrenergic receptor.

In light of the prior art the technical problem underlying the invention was the provision of means for specifically detecting these disease-associated agAAB and for treating dementia, preferably Alzheimer's disease or vascular dementia and stroke, that overcome the disadvantages of the prior art. This problem is solved by the features of the independent claims. Preferred embodiments of the present invention are provided by the dependent claims.

Therefore, an object of the invention is to provide a peptide, comprising of
  (i) the amino acid sequence LGYWAFGRVFCN (SEQ ID No. 1) or PAPEDETICQINEE (SEQ ID No. 2);

(ii) an amino acid sequence having a sequence with 70%, preferably 80% or more preferably 90% or 95% sequence identity to an amino acid sequence in accordance with (i);

(iii) an amino acid sequence (i) or (ii) which is modified by branch or extension with the same or another peptide according to amino acid sequence (i) or (ii) to form a homooligomeric or heterooligomeric peptide, whereby any terminus of the peptide according to i) to iii) exhibits an additional group selected from an amino group, amide group, acetyl group, biotin group, desthio-biotin group, a marker, spacer, linker, GKK, SGKK, or no additional group.

In one embodiment the peptide of the invention is for use in medical diagnostics or as a medicament.

In one embodiment the peptide of the invention is characterized in that the peptide binds to antibodies of patients suffering from dementia, preferably agonistic autoantibodies that bind the $\alpha_1$-adrenergic and/or the $\beta_2$-adrenergic receptor.

The invention further relates to an isolated nucleic acid molecule selected from the group comprising:
  a) a nucleic acid molecule consisting of a nucleotide sequence which encodes at least one peptide selected from the group consisting of peptides of the invention;
  b) a nucleic acid molecule which is complementary to a nucleotide sequence in accordance with a);
  c) a nucleic acid molecule which undergoes hybridization with a nucleotide sequence according to a) or b) under stringent conditions;
  d) a nucleic acid molecule consisting of a nucleotide sequence having a sequence with 90% sequence identity to a nucleotide sequence according to a), b) or c);
  e) a nucleic acid molecule which, as a consequence of the genetic code, is degenerated into a nucleotide sequence according to a) through d).

The invention further relates to a solid phase for affinity chromatography or solid-phase extraction, or an immunoassay, such as ELISA, consisting of organic, inorganic, synthetic polymers or of mixed polymers, preferably glass, plastic, cross-linked agarose, cellulose, silica gel, polyamide and polyvinyl alcohols, or other synthetic material, such as a bead, slide or micro-titer plate, which are optionally chemically activated, that comprise one or more peptides of the invention, immobilized on the surface of the solid phase.

The invention further relates to an affinity chromatography apparatus, such as a column, comprising one or more peptides or a solid phase of the invention for plasmapheresis and binding of autoantibodies which react with the $\alpha_1$-adrenergic and/or the $\beta_2$-adrenergic receptor or all IgG, preferably from whole blood or plasma.

The invention further relates to a recognition molecule that binds antibodies of patients suffering from dementia, preferably agonistic autoantibodies that bind the $\alpha_1$-adrenergic and/or the $\beta_2$-adrenergic receptor, more preferably autoantibodies that bind the peptides of SEQ ID no. 1 and/or 2, or other variants as described herein, preferably selected from the group comprising of antibodies, such as a therapeutic antibody, antisense constructs, chelating agents, aptamers or spiegelmers.

The invention further relates to a pharmaceutical composition comprising a peptide, a nucleic acid molecule, a solid phase and/or a recognition molecule as described herein, optionally together with a pharmaceutically tolerable carrier.

In a preferred embodiment the invention relates to a peptide, a nucleic acid molecule, a solid phase, a recognition molecule and/or a pharmaceutical composition as described herein for the diagnosis, therapy, prophylaxis or monitoring of disease progression of dementia.

The invention further relates to the use of a peptide, a nucleic acid molecule, a solid phase, an apparatus, a recognition molecule and/or a pharmaceutical composition as described herein, for the in vitro diagnosis of dementia.

The invention further relates to the use of a peptide, a nucleic acid molecule a solid phase, an apparatus, a recognition molecule and/or a pharmaceutical composition as described herein in the production or screening of a drug for the treatment of dementia.

In a preferred embodiment the peptide, nucleic acid molecule, solid phase, recognition molecule and/or pharmaceutical composition as described herein or the use of said peptide, nucleic acid molecule, solid phase, recognition molecule and/or pharmaceutical composition is characterized in that the dementia is Alzheimer's disease, vascular dementia, stroke or stroke-related dementia.

The invention further relates to a kit that comprises the peptide, a nucleic acid molecule, a solid phase, an apparatus, a recognition molecule and/or a pharmaceutical composition as described herein, for the in vitro diagnosis of dementia.

In one embodiment the kit of the invention comprising additionally of reagents for an enzyme-linked immunosorbent assay (ELISA) test, selected from the group comprising of slides, micro-titre plates, secondary antibodies, marker enzymes and/or corresponding marker enzyme substrate for antibody detection.

The invention further relates to the use of a specific ligand for human immunoglobulin in the manufacture of a column coupled to said ligand for the treatment of a patient suffering from dementia, said treatment comprising passing plasma of the patient, over the column under conditions which effect the binding of said specific ligand to immunoglobulin in the patient's plasma, thereby removing a significant portion of the immunoglobulin from the patient's plasma, and reinfusing the plasma to the patient.

In one embodiment the use according as described above of a specific ligand for human immunoglobulin is characterised in that
  said specific ligand is selected from the group consisting of polyclonal anti-human immunoglobulin antibodies, monoclonal anti-human immunoglobulin antibodies, a fragment of such antibodies, recombinant molecules of the antibody idiotype, synthesized peptides, Protein A and Protein G and
  removal of autoantibodies occurs, whereby the autoantibodies removed react with the $\alpha_1$-adrenergic and/or the $\beta_2$-adrenergic receptor, preferably removing a significant proportion of autoantibodies from the patients plasma that bind to the peptides described in the preceding claims.

The invention further relates to an in vitro method for binding and removing a portion of the immunoglobulin from plasma taken from a patient suffering from dementia, the method comprising
  a) providing a column coupled to a specific ligand for human immunoglobulin, and
  b) passing the plasma over the column under conditions which effect the binding of said specific ligand to immunoglobulin in the plasma.

The invention further relates to a method for the treatment of dementia, preferably Alzheimer's disease, vascular dementia, stroke or stroke-related dementia, comprising the administration of a therapeutically relevant amount of an agent selected from a peptide, a nucleic acid molecule, a solid phase, a recognition molecule and/or a pharmaceutical composition as described herein, to a patient in need thereof, either via administration of the agent in vivo to the patient or ex vivo use of the agent in an apharese- or chromatography-based therapeutic method.

The use of a specific ligand for human immunoglobulin in manufacturing a column, in addition to the method for removing total IgG, provides a surprising and advantageous approach in the treatment of dementia. It was unexpected, that a method that removes total IgG provides sufficient clearance (neutralization) of the specific agonistic autoantibodies associated with and causative for dementia. Further experiments have shown that sufficient removal of the pathological autoantibodies does occur via application of a column that removes total IgG, in particular IgG3, which is enriched for autoantibodies.

Preferred sequences of the invention are:

SEQ ID No. 1: LGYWAFGRVFCN

SEQ ID No. 2: PAPEDETICQINEE

BRIEF DESCRIPTION OF THE DRAWINGS

The figures provided herein represent examples of particular embodiments of the invention and are not intended to limit the scope of the invention. The figures are to be considered as providing a further description of possible and potentially preferred embodiments that enhance the technical support of one or more non-limiting embodiments.

Effect of peptides corresponding to extracellular loop1 (L1: LGYWAFGRVFCN) or extracellular loop2 (L2: PAPEDETICQINEE) of the $\alpha_1$-AR on the chronotropic response of spontaneously contracting neonatal cardiomyocytes to IgG preparations from AD/vascular dementia patients. Three patients were studied and were found to be exclusively sensitive to the L1 peptide. The chronotropic response to the application of patients' IgG was abolished by preincubation with the L1 peptide. The measurements of each patient were performed in triplicates and repeated up to four times. Data are given as means±SEM.

FIG. 3: Agonistic autoantibodies to the $\alpha_{1A}$-adrenergic receptor associated with Alzheimer's/vascular dementia mobilize cytosolic calcium (Ca$_i$) in CHO-$\alpha_1$ cells The data represent mean values of independent measurements of three individual cell populations. A: Time dependence of Ca$_i$ mobilization by patient IgG compared to the $\alpha_1$-AR agonist phenylephrine (PE). The addition of patient IgG preparation and PE is indicated by the arrow. The additions were (▲) 2.5 µg patient IgG; (■) 5 µg patient IgG; (●) 5 µM PE. B: Effect of 5 µg human control IgG (∆) and 5 µg patient IgG (◆) on Ca$_i$ mobilization. The addition of IgG preparations is indicated by the arrow. C: Inhibitory effect of preincubation of patient IgG with the free $\alpha_1$-AR loop1 peptide. Patient IgG was preincubated with 0.25 µM peptide for 15 minutes before addition to the cells. Peak values (five of each individual measurement) were taken for assessing the decrement in Ca$_i$ mobilization. Data are given as means±SEM (** $p<0.01$).

Analysis of serum samples from dement patients was performed using the E.R.D.E. GmbH in-house ELISA. Specific peptides of the $\beta_2$-adrenergic receptor Loop 1 ($\beta$2L1) and of the $\beta_2$-adrenergic receptor Loop 2 ($\beta$2L2) were used antigen. Ctr: control values with phosphate buffered saline, 1-6 serum samples of individual patients.

DETAILED DESCRIPTION OF THE INVENTION

Dementia is a decline of reasoning, memory, and other mental abilities (the cognitive functions). This decline eventually impairs the ability to carry out everyday activities. Dementia is most common in elderly people; it used to be called senility and was considered a normal part of aging. Dementia is however not a normal part of aging but is caused by a number of underlying medical conditions that can occur in both elderly and younger persons. The invention is based on the identification of particular autoantibodies that are present in dementia patients, which represents an underlying pathological cause. Dementia can be determined using routine tests known to those skilled in the medical field. Preferred subjects of the invention are those that have been shown to exhibit the agonistic autoantibodies described herein.

Alzheimer's disease (AD) is a common form of dementia and is a preferred disorder to be treated with the means of the present invention. AD is named after its discoverer Alois Alzheimer (1864-1915), is a progressive degenerative disease. It is characterized by changes in the cerebral cellular structure and function caused by deposits of aggregated proteins with extensive consequences for essential brain functions. The following clinical and cognitive characteristics are essential: disorders of the short-term memory at first and of the long-term memory later on, disorders of the perception of simple recognition patterns, progressive loss of speech and articulateness and progressive loss of sense of smell, of spatial orientation and decline of ability to perform routine tasks.

The diagnosis "AD" is obtained by different methods, for example, with imaging methods, such as computer tomography (CT) or magnetic resonance tomography (MRT) and by the chemical determination in the laboratory of the concentrations of the involved pathological molecules in the cerebrospinal fluid. Electroencephalography (EEG) may also be recurred to. Cognitive tests, such as the mini mental status test (MMST) are increasingly gaining importance.

Dementia, and in particular AD, is a "one-way street" which unavoidably results in a deterioration of the clinical image over several years to end with death. All therapeutical approaches adopted so far proved finally inefficient to stop the progression of the disease. The more advanced the stage of the disease, the more care and cost intensive the patient becomes.

Vascular dementia is dementia caused by problems in supply of blood to the brain. Multi-infarct dementia is one type of vascular dementia. Vascular dementia is the second most common form of dementia after Alzheimer's disease (AD) in older adults. Multi-infarct dementia (MID) is thought to be an irreversible form of dementia, and its onset is caused by a number of small strokes or sometimes, one large stroke preceded or followed by other smaller strokes. The main subtypes of this disease are: mild cognitive impairment, multi-infarct dementia, vascular dementia due to a strategic single infarct (affecting the thalamus, the anterior cerebral artery, the parietal lobes or the cingulate gyrus), vascular dementia due to hemorrhagic lesions, and mixed Alzheimer's and vascular dementia.

Vascular lesions can be the result of diffuse cerebrovascular disease, such as small vessel disease, or focal lesions; usually both. Mixed dementia is diagnosed when patients have evidence of AD and cerebrovascular disease, either clinically or based on neuroimaging evidence of ischemic lesions. In fact vascular dementia and Alzheimer's disease often coexist, especially in older patients with dementia.

MID is sometimes triggered by cerebral amyloid angiopathy, which involves accumulation of beta amyloid plaques in the walls of the cerebral arteries, leading to breakdown and rupture of the vessels. Since amyloid plaques are a characteristic feature of AD, vascular dementia may occur as a side effect of it. However, cerebral amyloid angiopathy can also appear in people with no prior dementia condition and a small amount of beta amyloid plaques are often present in cognitively normal older persons.

Considering the crucial importance of cerebrovascular lesions in vascular dementia, the term dementia additionally includes the stroke, preferably stroke-related dementia. Stroke is a disease of the blood vessels in and around the brain. It occurs when part of the brain does not receive enough blood to function normally and the cells die (infarction), or when a blood vessel ruptures (hemorrhagic stroke). Infarction is more common than haemorrhage and has a number of causes; for example, a vessel (artery) supplying blood to the brain can become blocked by a fatty deposit (plaque), which can form clots and send pieces into vessels further in the brain, or these arteries become thickened or hardened, narrowing the space where the blood flows (atherosclerosis). In addition, clots can arise in the heart and travel to the brain. Permanent damage to brain cells can result.

The symptoms of stroke vary, depending on which part of the brain is affected. Common symptoms of stroke are sudden paralysis or loss of sensation in part of the body (especially on one side), partial loss of vision or double vision, or loss of balance. Loss of bladder and bowel control can also occur. Other symptoms include decline in "cognitive" mental functions such as memory, speech and language, thinking, organization, reasoning, or judgment. Changes in behaviour and personality may occur. These symptoms are severe enough to interfere with everyday activities and represent a non-limiting embodiment of dementia.

Cognitive decline related to stroke is also known as vascular dementia or vascular cognitive impairment. In the United States, it is the second most common form of dementia after Alzheimer's Disease. People who have had a stroke have a 9 times greater risk of dementia than people who have not had a stroke. About 1 in 4 people who have a stroke develop signs of dementia within 1 year. Vascular dementia is most common in older people, who are more likely than younger people to have vascular diseases. It is more common in men than in women.

The invention discloses for the first time the presence of agAAB to the $\alpha_1$-AR and $\beta_2$-adrenergic receptor ($\beta_2$-AR) in patients with moderate to mild dementia of the AD and vascular type, which enables the inventive peptides of the present invention. The peptide targets of the agonistic pathogenic antibodies can subsequently be applied in neutralizing said unwanted antibodies, thereby providing a useful tool in the diagnosis and treatment of dementia, especially AD and vascular dementia.

Consequently, the peptides in the meaning of the invention can be designed in such a way and may include such a number of additional amino acids, spacers or other structures that they are suitable for interaction with the antibodies, and preferably in such a way that they represent an epitope for the latter.

Accordingly, the peptides according to the invention are not restricted to the sequences LGYWAFGRVFCN (SEQ ID NO: 1) or PAPEDETICQINEE (SEQ ID NO: 2), but rather, the peptides are preferably antibody epitopes essentially including the above-mentioned or functionally analogous sequences, so that they represent and characterize the epitope in such a way that the antibodies would undergo specific interaction with them. Therefore, under particular conditions the terms "epitope" and "peptide" may also be used synonymously.

Furthermore, it is possible to replace single amino acids or groups of amino acids without adversely affecting the activity of the peptides with respect to accomplishing the object of the present invention. For replacement of such amino acids, reference is made to appropriate standard textbooks of biochemistry and genetics.

Various ways of preparing peptides have been disclosed in the prior art. Peptides designed starting from the peptides of the invention using such methods are included in the teaching according to the invention. For example, one way of generating functionally analogous peptides has been described in PNAS USA 1998, Oct. 13, 9521, 12179-84; WO 99/6293 and/or WO 02/38592; and the above teachings are hereby incorporated in the disclosure of the invention. That is, all peptides, peptide fragments or structures comprising peptides generated using the methods mentioned above—starting from the peptides of the invention—are peptides according to the invention, provided they accomplish the object of the invention and, in particular, interact with the pathogenic autoantibodies. For example, these autoantibodies can be agonistic autoantibodies.

The peptides of the invention can be used with advantage in various fields of diagnosis and therapy of autoimmune diseases. Various ways of modifying peptides for various applications are well-known to those skilled in the art. If, for example, the peptides are envisaged to be administered as a drug, e.g. on the oral route, the structure of the peptides has to be changed in a specific fashion, as is well-known to those skilled in the art. However, the peptides may also be bound to the supporting material of an affinity column in order to be used in the purification of body fluids, especially blood plasma; binding of the peptides to a matrix requires specific structural modifications of the peptides according to the invention, and such modifications are also well-known to those skilled in the art and were used to develop a specific, two-step peptide-based ELISA, which is part of the invention.

As is well-known to those skilled in the art, some amino acids have analogous physicochemical properties so that these amino acids advantageously can be replaced by each other. For example, these include the group of amino acids (a) glycine, alanine, valine, leucine and/or isoleucine; or the amino acids (b) serine and threonine, the amino acids (c) asparagine and glutamine, the amino acids (d) aspartic acid and glutamic acid; the amino acids (e) lysine and arginine, as well as the group of aromatic amino acids (f) phenylalanine, tyrosine and/or tryptophan. Amino acids within one and the same group (a-f) can be replaced with one another. Furthermore, the amino acids can be replaced by modified amino acids or specific enantiomers. Further modifications are possible in accordance with the teaching of WO 99/62933 or WO 02/38592.

The term sequence identity refers to a similarity between multiple amino acid or nucleotide sequences, respectively, obtained by using computer-based sequence alignment tools, such as NCBI BLAST or Clustal from EBI. Sequence identity can be measured without undue effort by a skilled person.

In another preferred embodiment the peptide comprises a linker and/or a spacer selected from the group comprising .alpha.-aminocarboxylic acids as well as homo- and heterooligomers thereof, alpha-, omega-aminocarboxylic acids and branched homo- or heterooligomers thereof, other amino acids, as well as linear and branched homo- or heterooligomers (peptides); amino-oligoalkoxyalkylamines; maleinimidocarboxylic acid derivatives; oligomers of alkylamines; 4-alkylphenyl derivatives; 4-oligoalkoxyphenyl or 4-oligoalkoxyphenoxy derivatives; 4-oligoalkylmercaptophenyl or 4-oligoalkylmercaptophenoxy derivatives; 4-oligoalkylaminophenyl or 4-oligoalkylaminophenoxy derivatives; (oligoalkylbenzyl)phenyl or 4-(oligoalkylbenzyl)phenoxy derivatives, as well as 4-(oligoalkoxybenzyl)phenyl or 4-(oligoalkoxybenzyl)phenoxy derivatives; trityl derivatives; benzyloxyaryl or benzyloxyalkyl derivatives; xanthen-3-yloxyalkyl derivatives; (4-alkylphenyl)- or omega-(4-alkylphenoxy)alkanoic acid derivatives; oligoalkylphenoxyalkyl or oligoalkoxyphenoxyalkyl derivatives; carbamate derivatives; amines; trialkylsilyl or dialkylalkoxysilyl derivatives; alkyl or aryl derivatives and/or combinations thereof; other possible structures have been described in EP 1 214 350 which hereby is incorporated in the disclosure of the invention.

In another preferred embodiment of the invention the peptide is used or employed as a therapeutic active substance or medicament. In the meaning of the invention, the use as a therapeutic active substance or medicament means use of the peptide in the entire field of medicine.

In another particularly preferred embodiment of the invention the peptide is bound by specific antibodies of patients with dementia, especially by autoantibodies. At a defined quantity ratio of peptide and autoantibody, which is well-known to those skilled in the art, autoantibody-peptide complexes will form which, for example, undergo precipitation or exhibit specific reaction behaviour in a way so as to allow elimination of the autoantibodies.

In another preferred embodiment of the invention the peptide, in particular, is immobilized. In the meaning of the invention, immobilization is understood to involve various methods and techniques to fix the peptides on specific carriers, e.g. according to WO 99/56126 or WO 02/26292. For example, immobilization can serve to stabilize the peptides so that their activity would not be reduced or adversely modified by biological, chemical or physical exposure, especially during storage or in single-batch use. Immobilization of the peptides allows repeated use under technical or clinical routine conditions; furthermore, a sample—preferably blood components—can be reacted with at least one of the peptides according to the invention in a continuous fashion. In particular, this can be achieved by means of various immobilization techniques, with binding of the peptides to other peptides or molecules or to a carrier proceeding in such a way that the three-dimensional structure—particularly in the active centre mediating the interaction with the autoantibodies—of the corresponding molecules, especially of said peptides, would not be changed. Advantageously, there is no loss in specificity to the autoantibodies of the patient as a result of such immobilization. In the meaning of the invention, three basic methods can be used for immobilization:

(i) Crosslinking: in crosslinking, the peptides are fixed to one another without adversely affecting their activity. Advantageously, they are no longer soluble as a result of such crosslinking (ii) Binding to a carrier: binding to a carrier proceeds via adsorption, ionic binding or covalent binding, for example. Such binding may also take place inside microbial cells or liposomes or other membranous, closed or open structures. Advantageously, the peptides are not adversely affected by such fixing. For example, multiple or continuous use of carrier-bound peptides is possible with advantage in clinics in diagnosis or therapy.

(iii) Inclusion: inclusion in the meaning of the invention especially is inclusion in a semipermeable membrane in the form of gels, fibrils or fibres. Advantageously, encapsulated peptides are separated from the surrounding sample solution by a semipermeable membrane in such a way that interaction with the autoantibodies or fragments thereof still is possible.

Various methods are available for immobilization, such as adsorption on an inert or electrically charged inorganic or organic carrier. For example, such carriers can be porous gels, aluminum oxide, bentonite, agarose, starch, nylon or polyacrylamide. Immobilization proceeds via physical binding forces, frequently involving hydrophobic interactions and ionic binding. Advantageously, such methods are easy to handle, having little influence on the conformation of the peptides. Advantageously, binding can be improved as a result of electrostatic binding forces between the charged groups of the peptides and the carrier, e.g. by using ion exchangers such as Sephadex.

Another method is covalent binding to carrier materials. In addition, the carriers may have reactive groups forming homopolar bonds with amino acid side chains. Suitable groups in peptides are carboxy, hydroxy and sulfide groups and especially the terminal amino groups of lysines. Aromatic groups offer the possibility of diazo coupling. The surface of microscopic porous glass particles can be activated by treatment with silanes and subsequently coated with peptides. For example, hydroxy groups of natural polymers can be activated with bromocyanogen and subsequently coupled with peptides. Advantageously, a large number of peptides can undergo direct covalent binding with polyacrylamide resins. Inclusion in three-dimensional networks involves inclusion of the peptides in ionotropic gels or other structures well-known to those skilled in the art. More specifically, the pores of the matrix are such in nature that the peptides are retained, allowing interaction with the target molecules. In crosslinking, the peptides are converted into polymer aggregates by crosslinking with bifunctional agents. Such structures are gelatinous, easily deformable and, in particular, suitable for use in various reactors. By adding other inactive components such as gelatin in crosslinking, advantageous improvement of mechanical and binding properties is possible. In microencapsulation, the reaction volume of the peptides is restricted by means of membranes. For example, microencapsulation can be carried out in the form of an interfacial polymerization. Owing to the immobilization during microencapsulation, the peptides are made insoluble and thus reusable. In the meaning of the invention, immobilized peptides are all those peptides being in a condition that allows reuse thereof. Restricting the mobility and solubility of the peptides by chemical, biological or physical means advantageously results in lower process cost, particularly when eliminating autoantibodies from blood components.

The invention also relates to a pharmaceutical composition comprising the inventive nucleic acid molecules, vectors, host cells, peptides, optionally together with a pharmaceutically tolerable carrier. In particular, the pharmaceutical composition can be used as a drug. To this end, it is possible, for example, to modify the peptides by means of cyclization or other procedures well-known to those skilled in the art such that destruction thereof by endogenous peptide-degrading structures, e.g. serum proteases, is prevented. By using the peptides or recognition molecules according to the invention, in vivo or ex vivo neutralization of autoantibodies is possible. In in vivo neutralization, the drugs are administered directly to the patient; in ex vivo neutralization, the blood is conducted out of the body e.g. via a loop, e.g. in the form of a tube circulation, subsequently contacted with the drug and, following neutralization of the autoantibodies, resupplied into the organism, i.e., the patient. Regarded as drugs in the meaning of the invention are compositions for therapeutic and prophylactic purposes, as well as pharmaceutical compositions usable as diagnostic agents.

In particular, the apparatus according to the invention can be used to eliminate the autoantibodies from fluids of a patient or to neutralize the autoantibodies. This method is known to those skilled in the art under the term of immunoadsorption and apheresis therapy. With the aid of immunoadsorption, immunoglobulins are removed from the blood of a patient. Advantageously, this immunoadsorption treatment can be conducted in a stationary and ambulant fashion. It can be envisaged that the apparatus, particularly the so-called adsorber, is part of an extracorporeal blood circulation. To this end, blood is taken continuously or discontinuously from a patient's major vessel, particularly from an arm vein, and separated into single components, such as cellular and humoral components, using filtration or centrifugation. In particular, one essential blood component obtained in this fashion is blood plasma. Advantageously, the blood plasma can be passed through the apparatus of the invention and, following adsorption of the autoantibodies, returned into the patient, particularly through another vein of arms or legs, together with previously separated blood components, especially cellular components. It can also be envisaged that the peptides are immobilized on a Sepharose matrix. The matrix can be placed in a container having a volume of 10 to 400 ml. Thereafter, the blood plasma of the patient can be passed over the matrix where the autoantibodies will be bound, thus allowing elimination thereof from the blood plasma. Those skilled in the art will be familiar with various ways of providing such solid phase-fixed peptides, e.g. in the form of (i) regeneratable adsorption columns, (ii) double columns and (iii) disposable columns. The diverse wash and elution solutions, permitting high efficiency of treatment, can easily be determined by a person skilled in the art by using routine tests. By providing the teaching according to the invention, particularly the peptides of the invention, various ways of employing the peptides in vivo, ex vivo and in vitro in prophylaxis, diagnosis, therapy and aftercare of cold-induced, autoantibody-mediated diseases are disclosed to a person skilled in the art.

According to the invention, drugs or pharmaceutical compositions—used in a synonymous fashion herein—are substances and formulations of substances intended to cure, alleviate or avoid diseases, illness, physical defects or pathological affection by application on or in the human body. According to the invention, medical adjuvants are substances used as active ingredients in the production of drugs. Pharmaceutical-technical adjuvants serve to suitably formulate the drug or pharmaceutical composition and, if required during the production process only, can even be removed thereafter, or they can be part of the pharmaceutical composition as pharmaceutically tolerable carriers. Examples of pharmaceutically tolerable carriers will be given below. Drug formulation or formulation of the pharmaceutical composition is optionally effected in combination with a pharmaceutically tolerable carrier and/or diluent. Examples of suitable pharmaceutically tolerable carriers are well-known to those skilled in the art and comprise e.g. phosphate-buffered saline, water, emulsions such as oil/water emulsions, various types of detergents, sterile solutions, and so forth. Drugs or pharmaceutical compositions comprising such carriers can be formulated by means of well-known conventional methods. These drugs or pharmaceutical compositions can be administered to an individual at a suitable dose, e.g. in a range of from 1 .mu.g to 10 g of peptides per day and patient. Doses of from 1 mg to 1 g are preferred. Preferred is administration of doses as small in number and as low as possible, preferably a single dose. Administration can be effected on various routes, e.g. intravenous, intraperitoneal, intrarectal, intragastrointestinal, intranodal, intramuscular, local, e.g. intratumoral, but also subcutaneous, intradermal or on the skin or via mucosa. Administration of nucleic acids encoding the peptide according to the invention can also be effected in the form of a gene therapy, e.g. via viral vectors. The kind of dosage and route of administration can be determined by the attending physician according to clinical factors. As is familiar to those skilled in the art, the kind of dosage will depend on various factors such as size, body surface, age, sex, or general health condition of the patient, but also on the particular agent being administered, the time period and type of administration, and on other medications possibly administered in parallel. Those skilled in the art will also be familiar with the fact that the concentration of autoantibodies can be diagnosed first, using the peptides according to the invention, in order to determine the required concentration of drug.

More specifically, the pharmaceutical compositions or drugs comprise a pharmacological substance which includes one or more peptides or recognition molecules of the invention, or/and nucleic acid molecules encoding same, in a suitable solution or administration form. Administration thereof can be effected either alone or together with appropriate adjuvants described in connection with drugs or pharmaceutical compositions, or in combination with one or more adjuvants, e.g. QS-21, GPI-0100 or other saponines, water-oil emulsions such as Montanide adjuvants, polylysine, polyarginine compounds, DNA compounds such as CpG, Detox, bacterial vaccines such as typhoid vaccines or BCG vaccines, salts such as calcium phosphates, and/or other suitable material enhancing the effect. They are mixed with the peptides of the invention according to well-known methods and administered in suitable formulations and dosages. Formulations, dosages and suitable components are well-known to those skilled in the art.

Obviously, the pharmaceutical composition or drug can also be a combination of two or more of the inventive pharmaceutical compositions or drugs, as well as a combination with other drugs, such as antibody therapies, chemotherapies or radiotherapies, suitably administered or applied at the same time or separately in time. The production of the drugs or pharmaceutical compositions proceeds according to per se known methods.

A preferred embodiment of the invention is a recognition molecule directed against the peptides according to the invention, or directed against the agonistic autoantibodies characterised in the present invention. In a preferred fashion the recognition molecules are antibodies, antisense constructs and/or chelating agents. The recognition molecules according to the Invention can be antibodies directed against the autoantibodies inducing dementia. A skilled person is well-versed in the art of generating antibodies that bind a particular target. The preferred target of the antibodies of the present invention is an epitope of the dementia related autoantibody, whereby the recognition molecule, preferably antibody, binds in a specific manner, thereby neutralizing said autoantibody. These agonistic autoantibodies are directed against the α1-adrenergic receptor and the β2-adrenergic receptor. The interaction or reaction or binding of the autoantibody is a specific antigen-antibody-interaction. In a preferred embodiment the recognition molecules are antibodies, antisense constructs and/or chelating agents and/or aptamers or Spiegelmers. The recognition molecules according to the invention can be antibodies directed against the autoantibodies inducing dementia. It is also possible that the recognition molecule is a peptidomimetic. The term antibody is understood to encompass all antibody variations, such as poly- or monoclonal antibodies, in addition to modified antibody structures, such as fragments or short chain fragments of various antibody components, or modified antibody fragments, that exhibit the same properties of specific binding as an antibody.

An aptamer is a nucleic acid structure that can bind to a target molecule conceptually similar to an antibody that recognizes an antigen (Ellington & Szostak, 1990). Based on the SELEX (Systematic Evolution of Ligands by EXponential enrichment) process (Tuerk & Gold, 1990), aptamers can be identified from huge combinatorial nucleic acids libraries of up to >$10^{15}$ different sequences. The sequences in the library are comprised of a central randomized region flanked by fixed sequences that permit amplification by polymerase chain reactions (PCR). The library size depends on the length of the random portion of the molecule, creating a diverse universe of molecules ready for screening. The aptamers capable of binding to a target are then selected by incubating the libraries with the immobilized target, washing extensively, then eluting the bound aptamer. After amplification by PCR, these binding molecules are re-selected, eluted and amplified. By repeating this procedure multiple times, and eluting bound aptamers under progressively more stringent conditions, the molecules with greatest affinity and specificity are selected. Aptamers have binding characteristics similar to peptides or antibodies, with affinities in the low nanomolar to the picomolar range. Spiegelmers (Klussmann et al., 1996; Vater & Klussmann, 2003) are molecules, which are biostable aptamers, have all of the diversity characteristics of aptamers but possess a structure that prevents enzymatic degradation. While aptamers are created from the natural D-nucleotides, which are recognized by the nucleic acid degrading enzymes, a molecule synthesized as the mirror image L-oligonucleotide will not be degraded by any nuclease since there are no such enzymes in the body capable of interacting with these unnatural molecules.

A preferred embodiment of the invention relates to the use of the inventive peptides in an ELISA test for in vitro diagnosis or therapy control of dementia. The enzyme-linked immunosorbent assay (ELISA) is a popular format of an analytic biochemistry assay that uses one sub-type of heterogeneous, solid-phase enzyme immunoassay (EIA) to detect the presence of a substance, usually an antigen, in a liquid sample or wet sample.

One embodiment of the invention relates to fixing the antigen (in this case the target peptides of the present invention) to a surface. Then a biological fluid to be investigated, for example a blood or plasma sample, is provided and incubated with the fixed epitope. Subsequently any bound antibody (bound to the fixed epitope) is linked to an enzyme, and, in the final step, a substance containing the enzyme's substrate is added. The subsequent reaction produces a detectable signal, most commonly a colour change in the substrate. Various methods are possible for utilization of the inventive peptides in the ELISA setup. Secondary antibodies and marker enzymes and their appropriate substrates are commonly known to those skilled in the art. In the present case anti-human IgG secondary antibody could be applied in order to detect the agonistic autoantibodies associated with dementia, which have bound the inventive peptides, which are immobilized on a solid surface. Horseradish peroxidise is one non-limiting embodiment of a marker enzyme subsequently used to detect the secondary antibody.

EXAMPLES

The examples provided herein represent practical support for particular embodiments of the invention and are not intended to limit the scope of the invention. The examples are to be considered as providing a further description of possible and potentially preferred embodiments that demonstrate the relevant technical working of one or more non-limiting embodiments.

Analysis of Serum Samples from Patients

We identified agonistic autoantibodies directed at adrenergic receptors in the circulation of patients with mild to moderate Alzheimer's and vascular dementia. A cohort of 54 patients of both sexes with mild to moderate cognitive impairments due to AD or vascular dementia was recruited for the present study (Table 1). In 59% of these patients agonistic autoantibodies against the $\alpha_1$-adrenergic receptor extracellular loop 1 and the $\beta_2$-adrenergic receptor extracellular loops 1 and 2 were identified. In a control group of patients with neurological impairments others than Alzheimer's and vascular dementia, only 17% were found to harbor these autoantibodies.

TABLE 1

Prevalence of agonistic autoantibodies in patients with Alzheimer's/
vascular dementia
Identification of agonistic autoantibodies (agAAB) directed at
adrenergic receptors (AR) in sera from patients with mild to moderate
AD or vascular dementia (Dementia) and patients with neurological
impairments distinct to AD or vascular dementia (Controls). Given are
the numbers of bioassay-positive patients for agAAB to the
$\alpha_1$-adrenergic receptor ($\alpha_1$), to the $\beta_2$-adrenergic
receptor ($\beta_2$), and to both receptors ($\alpha_1 + \beta_2$).

|  | Number | Age (mean ± SD) | MMSE[1] (mean ± SD) | agAAB-positive for AR $\alpha_1$ | $\beta_2$ | $\alpha_1 + \beta_2$ |
|---|---|---|---|---|---|---|
| Dementia | 54 | 77 ± 10 | 23 ± 5 | 8 | 3 | 21 |
| Controls[2] | 12 | 83 ± 10 | n.d. | 1 | 0 | 1 |

[1]Mini-mental state examination
[2]This group includes patients with neurological impairments due to Parkinson's disease, delirium, alcohol abuse and other heterogenous causes. These patients showed no signs of dementia and were not scored by MMSE.
n.d.: not determined, In the age-related control group comprising patients with causes of cognitive impairments other than AD and vascular dementia, only 2 out of 12 patients (17%) reacted positively in the bioassay (Tab. 1). One of them harbored both $\alpha$1-AR and $\beta$2-AR agAAB species, whereas one patient was positive solely for $\alpha$1-AR. Thus, in patients with AD and vascular dementia there was an about 2.5-fold higher incidence of agAAB directed against the $\alpha$1-AR and the $\beta$2-AR.

For additional comparison, we analyzed a collective of 36 patients of both sexes at the age of (mean±SD) 67.8±3.2 years who were under outpatient treatment with myocardial complications but had no signs of cognitive impairments. None of these patients was positive for agAAB against the $\alpha$1-AR or the $\beta$2-AR, but 11 (31%) harbored agAAB directed at the $\beta$1-AR, which typically associate with dilated cardiomyopathy [16,17,18].

Identification agAAB Target Regions at the Receptor

Figure 1:
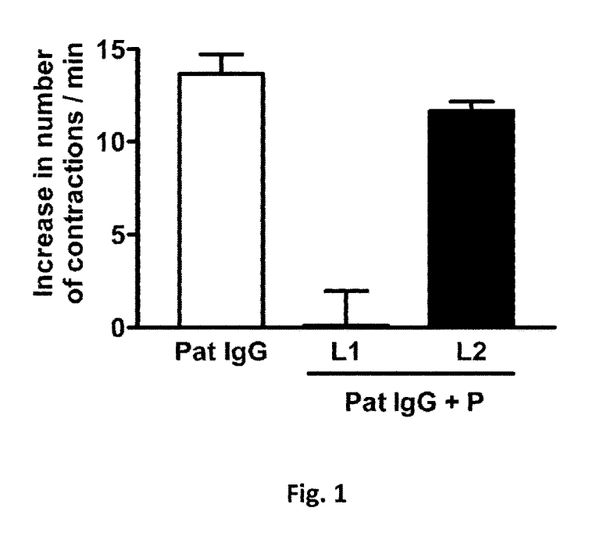
FIG. 1: Agonstic autoantibodies to the $\alpha_{1A}$-adrenergic receptor associated with Alzheimer's/vascular dementia are directed at the extracellular loop 1

Hypertension associated agAAB against the $\alpha$1-AR described so far bind to the extracellular loop1 or loop2 of the receptor [11,19]. To identify the target extracellular loops we examined IgG preparations from three AD/vascular dementia patients positive for agAAB to the ct1-AR in the cardiomyocyte contraction assay. In all three cases the chronotropic response was nearly abolished by preincubation of the IgG fraction with the loop1 peptide (FIG. 1). Preincubation with the loop2 peptide did not affect the chronotropic response to the application of patient IgG.

Functional Properties of agAAB to the $\alpha$1-AR in Patient IgG Preparations

Extensive studies of agAAB from patients are hampered by the small volumina of serum samples routinely obtained for diagnostics. However, column regenerates from immunoadsorption provided sufficient quantities of IgG to study the agAAB to the $\alpha$1-AR of the same patient in more detail. The patient who underwent immunoapheresis showed clinical signs of mild vascular dementia with a MMSE score of 23. In the bioassay the patient was positive for agAAB to the $\alpha$1-AR, but negative for $\beta$2-AR agAAB.

Binding Studies

Figure 2:
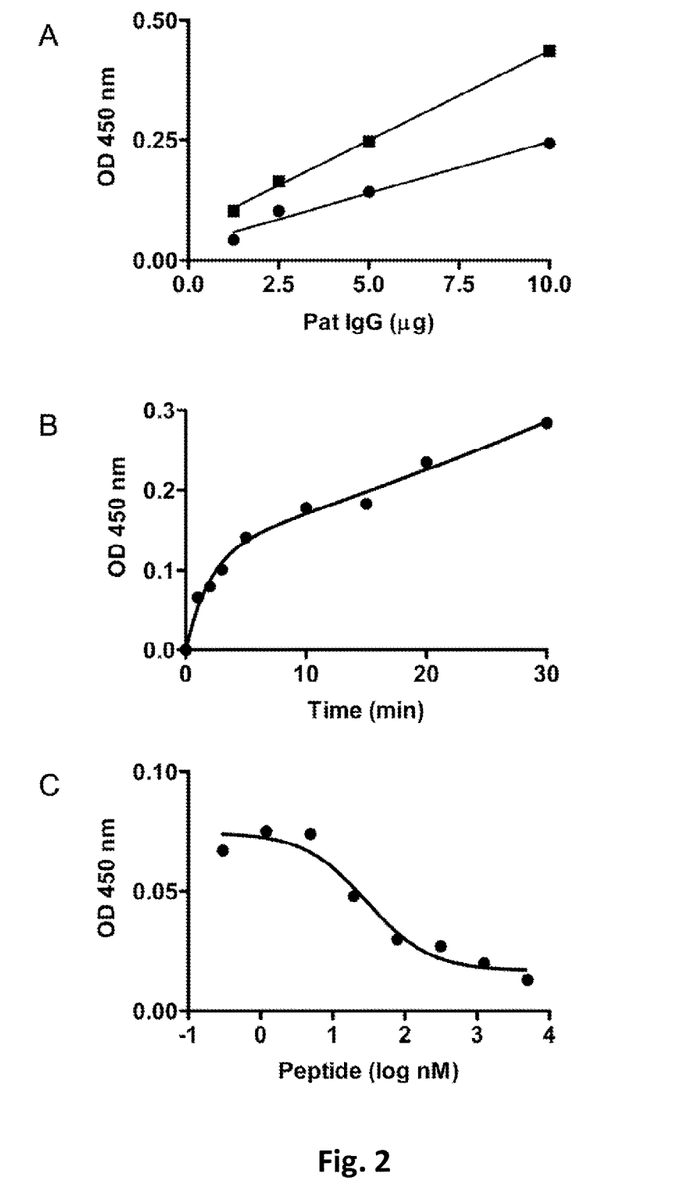
FIG. 2: Binding of patient IgG preparation to the immobilized $\alpha$1-AR loop1 peptide Shown are data from representative experiments run in triplicates. Values are corrected for unspecific binding. A: Dependence of antibody binding on patient IgG protein. The given amount of IgG protein refers to 100 µl reaction volume (□) binding in the presence of 0.15 M NaCl; (●) binding in the presence of 0.5 M NaCl. B: Time-dependence of antibody binding. C: Competition of binding by increasing concentrations of the free $\alpha$1-AR loop1 peptide. Concentrations of the free peptide ranged from 0.3 nM to 5.0 µM. The patient IgG was preincubated with the free peptide in solution for 15 minutes.

Studies of the dependence of patient IgG binding on protein and time confirmed the presence of patients agAAB specific towards the first extracellular loop peptide of the $\alpha$1-AR. There was almost no detectable binding to the second extracellular loop peptide. The binding to the first extracellular loop peptide of the $\alpha$1-AR was linear up to 10 μg of IgG protein (FIG. 2A). The assessment of binding at 0.15 M and 0.5 M sodium chloride revealed that the patient's $\alpha$1-AR agAAB pool consisted of antibodies with different avidity. In the presence of 0.5 M sodium chloride binding was suppressed by about 40% compared to 0.15 M sodium chloride. The time course of binding typically showed a faster initial phase and slower second phase (FIG. 2B). It was best described by a two phase exponential association with rate constants for the initial phase in the range of 0.5 min-1. In competition experiments using increasing concentrations of the soluble $\alpha$1-AR loop 1 peptide from 0.3 nM up to 5 μM the IgG binding to the immobilized peptide was reduced dose-dependently (FIG. 2C). Nonlinear regression gave approximations of the EC50 value of about 30 nM.

Effect on Intracellular Calcium

Figure 3:
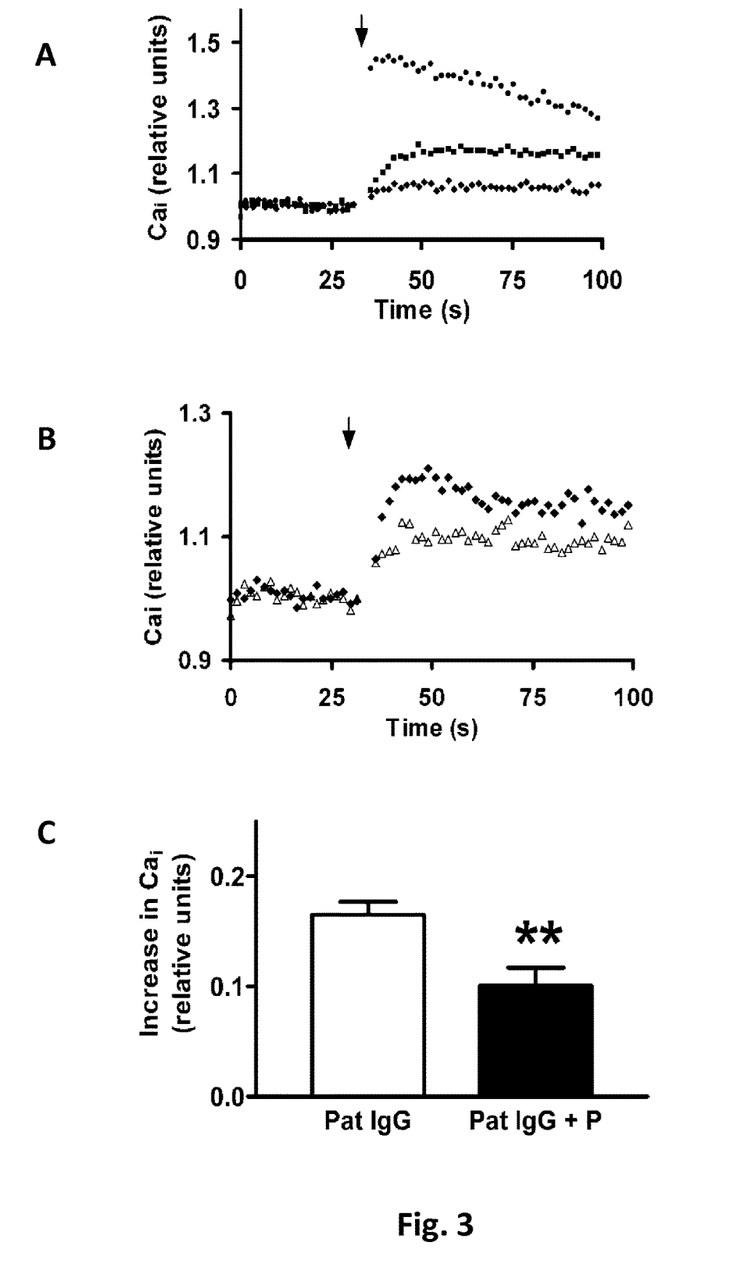

CHO-ct1 cells stably expressing the human $\alpha$1-AR were used to study the potential of patient IgG to affect Cai. Preliminary experiments demonstrated the efficient coupling of $\alpha$1-AR activation to Cai mobilization in these cells. FIGS. 3A and 3B show the effect of patient IgG on Cai in comparison with $\alpha$1-AR activation by its agonist phenylephrine (PE). The application of patient IgG resulted in a rise of Cai.

To test whether the increment in Cai caused by patient IgG requires the interaction with the $\alpha$1-AR, the antibody preparation was preincubated with the $\alpha$1A-AR loop 1 peptide. The peptide itself had no effect on Cai in CHO-$\alpha$1 A. Preincubation with the peptide reduced significantly the elevation of Cai by patient IgG demonstrating the $\alpha$1A-AR-specific component of the patient IgG action (FIG. 3C). However, there was a substantial remaining Cai mobilization suggesting an $\alpha$1-AR-independent mechanisms by either other constituents of the patient IgG pool or a more complex mode of action of the agAAB.

Agonistic Autoantibodies to the $\beta_2$-Adrenergic Receptor Associated with Alzheimer's/Vascular Dementia are Directed at the Extracellular Loop 1 or the Extracellular Loop 1 and the Extracellular Loop 2

Figure 4:
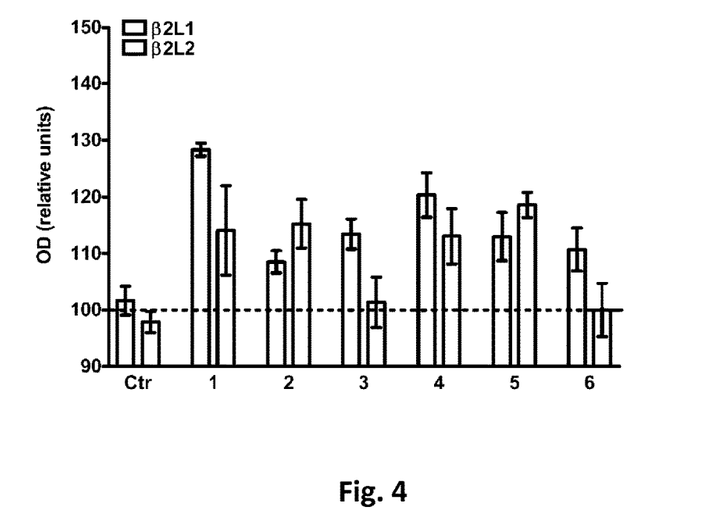
FIG. 4: Agonistic autoantibodies to the $\beta_2$-adrenergic receptor associated with Alzheimer's/vascular dementia are directed at the extracellular loop 1 or the extracellular loop 1 and the extracellular loop 2

Analysis of serum samples from dement patients was performed using the E.D.E. GmbH in-house ELISA. Specific peptides of the $\beta_2$-adrenergic receptor Loop 1 ($\beta$2L1) and of the $\beta_2$-adrenergic receptor Loop 2 ($\beta$2L2) were used as antigen. Analysis of the serum of the individual patients shows that patients 1, 2, 4 and 5 exhibited autoantibodies directed against both $\beta$2L1 and $\beta$2L2, whereas patients 3 and 6 exhibited autoantibodies against $\beta$2L1 (FIG. 4).

Specificity of Agonistic Autoantibodies to the $\beta_2$-Adrenergic Receptor Associated with Alzheimer's/Vascular Dementia for Receptor Loop 1 and Loop 2.

Analysis of serum samples from dement patients was performed using the E.R.D.E. GmbH in-house ELISA (Table 2). Specific peptides of the $\beta_2$-adrenergic receptor Loop and of the $\beta_2$-adrenergic receptor Loop 2 were used antigen. Loop 1+Loop 2 gives the number of dement patients harboring antibodies to both receptor loops.

TABLE 2

| | Agonistic autoantibodies to the $\beta_2$-adrenergic receptor | | |
|---|---|---|---|
| Patients | Loop 1 | Loop 2 | Loop 1 + Loop 2 |
| 14 | 5 | 0 | 9 |

Discussion of Experimental Examples

Here we report on the presence of a specific class of agAAB specifically interacting with adrenergic GPCR in sera from patients with AD and vascular dementia. We identified these antibodies to be directed against the α1-AR and the β2-AR. AgAAB to the α1A-AR were found in patients suffering from widespread diseases such as different types of hypertension, type 2 diabetes, and, as demonstrated here for the first time, in AD and vascular dementia [6,7, 11,14,19].

Interestingly, agAAB to the α1-AR associated with AD and vascular dementia recognized loop1 of the α1-AR. This suggests at least a preference of agAAB associated with AD and vascular dementia for the extracellular loop1 of the α1-AR. For comparison, in refractory hypertension the specificity of α1-AR agAAB were with 24% and 27% nearly equally distributed between the first and second extracellular loop, respectively [11]. AgAAB to the β2-AR were only found in combination with α1-AR agAAB, whereas the latter also occurred alone (in 20% of agAAB-positive patients). A link between these agAAB with respect to the time of their occurrence may be apparent.

AR have been shown to have the potential to damage the vasculature [13]. The availability of larger quantities of IgG from the column effluent of immunoadsorption enabled us to exemplarily study properties of the agAAB. The patient IgG elicited binding affinities towards its receptor loop peptide in the nanomolar range comparable to agAAB specific for the second extracellular loop of the α1-AR found in patients with refractory hypertension and to an antibody raised in rabbits [11,20]. The data shown herein from measurements of Cai gave evidence for the presence of a α1-AR-specific Cai raising component in the patient IgG preparation. The α1-AR-specific agAAB apparently mobilize Cai from the same source as the receptor agonist PE.

The data shown herein obtained with preparations containing the broad spectrum of patient IgG suggest a complex action on Cai. Certain kinds of cell membrane Fc receptors couple to Cai and may contribute to the effects observed with IgG preparations [21]. Thus, agAAB to the α1-AR found in patients with AD and vascular dementia may be considered candidate pathomolecules contributing to vascular lesions, which are of crucial importance in the pathogenesis and progression of the disease. Furthermore, increased Cai can facilitate amyloid toxicity in neurons by accelerating amyloid-β formation which in turn leads to a progressive calcium overload finally resulting in cell death [22].

The second agAAB species identified in sera of AD and vascular dementia patients was directed at the β2-AR. These agAAB identified in patients stimulates the β2-AR mimicking the physiological agonist. The β2-AR was recently shown to regulate the protease γ-secretase that in sequential reactions with β-secretase cleaves the amyloid-β precursor protein (APP) to the putative neurotoxic amyloid-β [1]. The authors correlated chronic β-AR stimulation with increased plaque formation in an AD mouse model. Considering their longer biological halflife and their capability to disable cellular protective mechanisms, agAAB to GPCR may nearly permanently activate the target receptor, resulting in the case of the neuronal β2-AR in enhanced plaque formation [17].

The contribution of autoimmunity to the pathology of dementia, both of the AD and the vascular type, has been an issue of controversy [23]. The brain belongs to the immune privileged organs of the body. A nearly ubiquitous occurrence of brain-reactive autoantibodies in human sera was reported, independent of any diseases [24]. Postmortem immunostaining studies showed the penetration of IgG into the brain parenchyma of AD patients [25]. This implicates a preceding impairment of the blood-brain barrier (BBB) that autoantibodies require to penetrate. Vascular impairments caused by agAAB to the α1A-AR may contribute to compromise the BBB. This in turn would favour the penetration of β2-AR agAAB to attack the receptor in neurons. Furthermore, vascular lesions are likely to decrease the clearance of β-amyloid from the central nervous system, thereby increasing the progression of the disease [26].

Investigations on post mortem brain tissue from AD patients led to the suggestion, that IgG binding to the target neurons precedes morphological changes [25]. Thus the detection of the potentially pathogenic agAAB provides a valuable early marker to assess the risk for patients to develop dementia. This underscores the importance of adequate diagnostics. Consequently, therapeutic strategies to specifically fight the action of agAAB may be employed. It was demonstrated that receptor antagonists are potent to abolish the action of agAAB thereby preventing end organ damages [10,18]. Antagonists of the α1-AR are in therapeutic use, e.g. in the treatment of benign prostate hyperplasia. However, they show diverse side effects. Clinically available antagonists specific to the β2-AR are still lacking. A more costly but highly efficient strategy is immunoadsorption. It has been applied in patients with dilated cardiomyopathy and refractory hypertension with significant improvements of the clinical signs [11,27,28].

In summary, the data provided in the examples of the invention demonstrates the presence of agAAB against the α1-AR and the β2-AR in patients diagnosed to suffer from AD and vascular dementia. The data characterizes agAAB to the α1-AR to interact with the extracellular loop1 with properties comparable to agAAB described in hypertension. The invention demonstrates that these autoantibodies are pathomolecules contributing to vascular lesions and increased plaque formation, two key factors in the pathogenesis and progression of AD and vascular dementia. Additionally, further experimentation shows that the preferred embodiments of the invention provide surprising and unexpected effects, thereby solving the problem of the invention in a non-obvious fashion.

Patients and Methods

Patients Material

Serum samples from patients with AD and vascular dementia and from patients with neurological impairments of other causes than dementia were kindly provided by Prof. Steinhagen-Thiessen, Hospital of Internal Medicine/Geriatrics, Innere Medizin/Geriatrics, Virchow-Clinics, Humboldt-University Berlin. A third cohort of patients investigated in the present study was from the German Heart Center, Berlin. These were outpatients with myocardial complications of different severity but no neurological and no signs of cognitive defects.

The column regenerate of a α1-AR agAAB positive patient with clinical signs of mild dementia who underwent immunoapheresis was kindly provided from Dr. Kassner, Hospital of Internal Medicine/Geriatrics, Innere Medizin/ Geriatrics, Virchow-Clinics, HumboldtUniversity Berlin. The regenerate containing the total spectrum of patient's IgG at a concentration of about 2 mg protein per ml. For further use, aliquots of the regenerate were desalted and pre-buffered to phosphate buffered saline containing 150 mM NaCl (PBS) on PD-10 columns and concentrated on Sartorius Vivaspin 500 concentrators to about the initial protein concentration. The patient IgG was aliquoted and stored at −20° C.

Cell Cultures

Cultures of neonatal cardiomyocytes were prepared from new-born, one to three days old rats essentially as described in [15]. Chinese hamster ovary cells stably transfected with the A-isoform of the human α1-AR (CHO-α1) were grown in F12 HAM medium supplemented with glutamine, 10% FCS and 1% penicillin streptomycin at 37° C. and 5% CO2.

Detection of Agonistic Autoantibodies

Functional autoantibodies were detected utilizing the chronotropic responses of cultivated spontaneously contracting neonatal cardiomyocytes [16]. For monitoring the contraction rate of neonatal cardiomyocytes a standardized bioassay based on computer-assisted recording of the contraction rate was employed.

Immunoglobulin (IgG) fractions from serum samples were prepared according to a standard procedure as described in [6]. Patients IgG were added to cultures of neonatal cardiomyocytes to a final dilution of 1:40. After incubation at 37° C. for 60 minutes, the pulsation rate was measured. A total of up to 30 cells or cell clusters for each sample of a given immunoglobulin fraction was analysed. The chronotropic response to the exposition to patient IgG compared to preceding control recordings is given as increases in the number of contractions per minute. Identification of the target GPCR type was performed using specific receptor antagonists, 10-7 M prazosin to block the α1-AR and 10-7 M ICI 188.551 for the β2-AR.

Assessment of the Receptor Target Site

For mapping of the target site of agonistic autoantibodies on the receptor, IgG fractions were preincubated for 1 hour at 4° C. with an excess of synthetic peptides corresponding to amino acid sequences of the extracellular loop1 (LGYWAFGRVFCN) or the extracellular loop2 (PAPEDETICQINEE) of the human α1-AR (1 µg peptide per 1 µg IgG protein).

Binding Experiments

The binding of agonistic IgG preparations was characterized using standard ELISA techniques. Briefly, biotinylated peptides corresponding to either the first or the second extracellular loop of the human α1A-AR were coupled to pre-blocked streptavidin-coated 96-well plates (Pierce). All experimental steps were performed at room temperature. If not indicated otherwise, 5 µg of IgG protein was used and the incubation time was 30 minutes. As secondary antibody anti-human horseradish conjugated anti-IgG was used. The antibody binding was visualized by the 1-Step Ultra TMB ELISA (Thermo Scientific). The optical density was quantified at 450 nm using a SLT Spectra multiplate reader (TECAN).

Analysis of Intracellular Calcium

The potential of patients IgG fractions to mobilise intracellular calcium (Cai) was assessed using Chinese hamster ovary cells stably transfected with the A-isoform of the human α1-AR (CHO-α1). The cells were trypsinized and plated on black clear bottom 96-well plates suited for fluorescence measurements (Greiner) at a density of 30 000 cells per well. Next day the medium was replaced by Hank's balanced salt solution (HBSS) buffered with 10 mM HEPES at pH 7.4 and incubated at 37° C. for one hour. Then cells were loaded with 5 µM FURA 2-AM or FURA PE3 in the presence of 2.5 mM probenecid for 45 minutes at room temperature. After rinsing with HBSS the cells were left for another 30 minutes to complete the enzymatic cleavage of the dye ester. Cai was measured on a Perkin Elmer Victor X2 fluorescence multiplate reader equipped with an injector unit. The cells were excited at wave lengths alternating between 340 nm and 380 nm and the fluorescence signal emitted at 510 nm was recorded. Baseline Cai of unstimulated cells was normalized to correct for variations between cell preparations. Data are given as relative units derived from the 340 nm/380 nm signal ratio.

REFERENCES

1 Ni Y, Zhao X, Bao G, et al. Activation of beta2-adrenergic receptor stimulates gamma-secretase activity and accelerates amyloid plaque formation. Nat Med 2006; 12:1390-1396.

2 Xu W, Qiu C, Gatz M, Pedersen N L, Johansson B, Fratiglioni L. Mid- and late-life diabetes in relation to the risk of dementia: a population-based twin study. Diabetes. 2009; 58:71-77.

3 Breteler M M. Vascular risk factors for Alzheimer's disease: an epidemiologic perspective. Neurobiol Aging 2000; 21:153-160.

4 De la Torre. Alzheimer disease as a vascular disorder: nosological evidence. Stroke 2002; 33:1152-1162.

5 Desmond D W, Moroney J T, Sano M, Stern Y. Incidence of dementia after ischemic stroke. Results of a longitudinal study. Stroke 2002; 33:2254-2262.

6 Luther H-P, Homuth V, Wallukat G. α1-adrenergig receptor antibodies in patients with primary hypertension. Hypertension 1997; 29:678-682.

7 Liao Y-H, Wei Y-M, Wang M, Wang Z-H, Yuan H-T, Cheng L-X. Autoantibodies against the AT1-receptor and α1-adrenergic receptor in patients with hypertension. Hypertens Res 2002; 25:641-646.

8 Wallukat G, Homuth V, Fischer T et al. Patients with preeclampsia develop agonistic autoantibodies against the angiotensin $AT_1$ receptor. J Clin Invest 1999; 103:945-95.

9 Jahns R, Boivin V, Hein L et al. Direct evidence for a β1-adrenergic receptor-directed autoimmune attack as a cause of idiotypic dilated cardiomyopathy. J Clin Invest 2004; 113:1419-1429.

10 Zhou C C, Zhang Y, Irani R et al. Angiotensin receptor agonistic autoantibodies induce pre-eclampsia in pregnant mice. Nat Med 2008; 14:855-862.

11 Wenzel K, Haase H, Wallukat G et al. Potential functional relevance of α1-adrenergic receptor autoantibodies in refractory hypertension. PLoS ONE 2008; 3:e3742.

12 Zhou Z, Liao Y-H, Wei Y et al. Cardiac remodelling after long-term stimulation by antibodies against the α1-adrenergic receptor in rats. Clin Immunol 2005; 114:164-173.

13 Zhou Z, Liao Y, Li L et al. Vascular damages in rats immunized by alpha1-adrenoceptor peptides. Cell Mol Immunol. 2008; 5:349-56.

14 Hempel P, Karczewski P, Kohnert K-D et al. Sera from patients with type 2 diabetes contain agonistic autoantibodies against G protein-coupled receptors. Scand J Immunol 2009; 70:159-160.

15 Halle W, Wollenberger A. Differentiation and behaviour of isolated embryonic and neonatal heart cells in a chemically defined medium. Am J Cardiol 1970; 25:292-299.

16 Wallukat G, Wollenberger A, Morwinski R, Pitschner H F. Anti-beta 1-adrenoceptor autoantibodies with chronotropic activity from the serum of patients with dilated cardiomyopathy: mapping of epitopes in the first and second extracellular loops. J Mol Cell Cardiol 1995; 27:397-406.

17 Magnusson Y, Wallukat G, Waagstein F, Hjalmarson A, Hoebeke J. Autoimmunity in idiopathic dilated cardiomyopathy: Characterization of antibodies against the β1-adrenoceptor with positive chronotropic effect. Circulation 1998; 89:2760-2767.

18 Wallukat G, Morwinski R, Magnusson Y, Hoebek J, Wollenberger A. Autoantikörper gegen den β1-adrenergen Rezeptor bei Myokarditis and dilatativer Kardiomyopathie: Lokalisation von zwei Epitopen. Z Kardiol 1992; 81:Suppl 4, 79-83.
19 Fu M L X, Herlitz H, Wallukat G et al. A Functional autoimmune epitope on $\alpha_1$-adrenergic receptors in patients with malignant hypertension. Lancet 1994; 344: 1660-1663.
20 Karczewski P, Haase H, Hempel P, Bimmler M. Agonistic antibody to the α1-adrenergic receptor mobilizes intracellular calcium and induces phosphorylation of a cardiac 15-kDa protein. Mol Cell Biochem 2010; 333:233-242.
21 Daeron M. FC receptor biology. Annu. Rev. Immunol. 1997; 15:203-234.
22 Demuro A, Parker I, Stutzmann G E. Calcium signaling and amyloid toxicity in Alzheimer disease. J Biol Chem 2010; 285:12463-12468.
23 Arshaysky Y I. Alzheimer's disease, brain immune privilege and memory: a hypothesis. J Neural Transm 2006; 113:1697-1707.
24 Levin E C, Acharya N K, Han M et al. Brain-reactive autoantibodies are nearly ubiquitous in human sera and may be linked to pathology in the context of blood-brain barrier breakdown. Brain Res 2010; 1345:212-232.
25 D'Andrea M R. Evidence linking neuronal cell death to autoimmunity in Alzheimer's disease. Brain Res 2003; 982:19-30.
26 Bowman G L, Kaye J A, Moore M, Waichunas, Carlson N E, Quinn J F. Blood-brain barrier impairment in Alzheimer disease. Stability and functional significance. Neurology 2007; 68:1809-1814
27 Mawuenyega K G, Sigurdson W, Ovod V et al. Decreased clearance of CNS β-amyloid in Alzheimer's disease. Science 2010; 330:1774.
28 Müller J, Wallukat G, Dandel M et al. Immunoglobulin adsorption in patients with idiopathic dilated cardiomyopathy. Circulation 2000; 101:385-391.
29 Staudt A, Schaper F, Stangl V, et al. Immunohistological changes in dilated cardiomyopathy induced by immunoadsorption therapy and subsequent immunoglobulin substitution. Circulation 2001; 103: 2681-2686.

What is claimed is:

1. A method of detecting agonistic autoantibodies that bind the a1-adrenergic receptor in a biological fluid in a human subject, the method comprising:
    (A) obtaining a sample of the biological fluid from the subject; and
    (B) conducting an assay on the sample, said assay comprising:
        (1) exposing the sample to a peptide, said peptide consisting of:
            (i) the amino acid sequence LGYWAFGRVFCN (SEQ ID No. 1) or PAPEDETICQINEE (SEQ ID No. 2); or
            (ii) an amino acid sequence (i) which is modified by branch or extension with the same or another peptide according to amino acid sequence (i) to form a homooligomeric or heterooligomeric peptide,
        wherein at least one terminus of the peptide according to (i) or (ii) exhibits an additional group selected from the group consisting of an amide group, an acetyl group, a biotin group, a desthiobiotin group, a marker, a peptide consisting of sequence GKK, and a peptide consisting of sequence SGKK (SEQ ID NO: 3); and (2) detecting binding of the peptide to agonistic autoantibodies that bind the α1-adrenergic and/or the β2-adrenergic receptor in the biological fluid.

2. A method for the treatment of dementia in a human subject, comprising:
(A) obtaining a sample of biological fluid from the subject;
(B) conducting an assay on the sample, said assay comprising
(1) exposing the sample to a peptide, said peptide selected from the group consisting of:
(i) the amino acid sequence LGYWAFGRVFCN (SEQ ID No. 1) or PAPEDETICQINEE (SEQ ID No. 2);
(ii) an amino acid sequence (i) which is modified by branch or extension with the same or another peptide according to amino acid sequence (i) to form a homooligomeric or heterooligomeric peptide,
wherein at least one terminus of the peptide according to (i) or (ii) exhibits an additional group selected from the group consisting of an amide group, an acetyl group, a biotin group, a desthiobiotin group, a marker, a peptide consisting of sequence GKK, and a peptide consisting of sequence SGKK (SEQ ID NO: 3); and
(2) detecting binding of the peptide to agonistic autoantibodies that bind the α1-adrenergic and/or the β2-adrenergic receptor in the biological fluid, wherein detection of said binding indicates the presence of dementia in the subject; and
(C) treating the subject for dementia.

3. The method according to claim 2, wherein the dementia is Alzheimer's disease.

4. The method according to claim 2, wherein the dementia is vascular dementia.

5. The method according to claim 2, wherein the dementia is stroke-related dementia.

6. The method according to claim 2, further comprising providing a solid phase comprising organic, inorganic, synthetic polymers or mixed polymers, wherein said solid phase comprises one or more peptides according to claim 2, and said peptides are immobilized on the surface of the solid phase.

7. The method according to claim 6, wherein the organic, inorganic, synthetic polymers or mixed polymers are selected from the group consisting of glass, plastic, cross-linked agarose, cellulose, silica gel, a polyamide and a polyvinyl alcohol and another synthetic material.

8. The method according to claim 7, wherein the synthetic material is selected from the group consisting of an optionally chemically activated bead, a slide and a micro-titer plate.

9. The method according to claim 2, wherein a kit is provided that comprises the peptide according to claim 2.

10. The method according to claim 9, wherein the kit additionally comprises reagents for an enzyme-linked immunosorbent assay (ELISA) test, selected from the group consisting of slides, micro-titer plates, secondary antibodies, marker enzymes and corresponding marker enzyme substrate for antibody detection.

11. The method according to claim 2, wherein the peptide is fixed to a surface, and wherein the method further comprises the following steps:
linking said agonistic autoantibodies bound to the fixed peptide to an enzyme; and
providing a substrate of the enzyme to the enzyme linked to the agonistic autoantibodies and detecting a signal produced from the enzyme interacting with its substrate.

12. The method according to claim 11, wherein the biological fluid is a blood or plasma sample.

13. The method according to claim 2, wherein treating the subject for dementia comprises passing plasma of the patient over a column, wherein said column is coupled to a specific ligand for human immunoglobulin, under conditions which effect the binding of said specific ligand to immunoglobulin of the patient's plasma, thereby removing a significant portion of the immunoglobulin from the patient's plasma, and reinfusing the plasma to the patient.

14. The method according claim 13, wherein:
said specific ligand is selected from the group consisting of polyclonal anti-human immunoglobulin antibodies, monoclonal anti-human immunoglobulin antibodies, a fragment of such antibodies, recombinant molecules of the antibody idiotype, synthesized peptides, Protein A and Protein G, and
removal of autoantibodies occurs, whereby the autoantibodies removed react with the α1-adrenergic and/or the β2-adrenergic receptor.

15. The method according to claim 2, wherein treating the subject for dementia comprises administering a therapeutically relevant amount of a peptide according to claim 2 (B)(1) to a patient in need thereof, either via administration of the agent in vivo to the patient or ex vivo use of the agent in an apharese-based therapeutic method.

* * * * *

UNITED STATES PATENT AND TRADEMARK OFFICE
CERTIFICATE OF CORRECTION

PATENT NO. : 9,708,372 B2
APPLICATION NO. : 14/749408
DATED : July 18, 2017
INVENTOR(S) : Marion Bimmler et al.

It is certified that error appears in the above-identified patent and that said Letters Patent is hereby corrected as shown below:

In Column 5 at Line 3, Change "apharese-" to --apherese- --.

In Column 5 at Line 31, Change "Agonstic" to --Agonistic--.

In Column 10 at Line 16, After "crosslinking" insert --.--.

In Column 15 at Line 19 (approx.), Change "heterogenous" to --heterogeneous--.

In Column 17 at Line 52, Change "3-AR" to --β-AR--.

In Column 18 at Line 6, Change "3-amyloid" to --β-amyloid--.

In Column 21 at Line 67, After "1809-1814" insert --.--.

In Column 22 at Line 48, In Claim 1, change "a1-adrenergic" to --α1-adrenergic--.

In Column 23 at Line 17 (approx.), In Claim 2, change "2);" to --2); and--.

In Column 24 at Line 1, In Claim 7, change "polyamide and" to --polyamide,--.

In Column 24 at Line 34 (approx.), In Claim 14, change "according claim" to --according to claim--.

In Column 24 at Line 49 (approx.), In Claim 15, change "apharese-based" to --apherese-based--.

Signed and Sealed this
Eighteenth Day of September, 2018

Andrei Iancu
*Director of the United States Patent and Trademark Office*